(12) United States Patent
Poeschl et al.

(10) Patent No.: US 8,485,144 B2
(45) Date of Patent: Jul. 16, 2013

(54) INTERNAL COMBUSTION ENGINE WITH A CYLINDER BLOCK AND A CYLINDER HEAD

(75) Inventors: Robert Poeschl, Graz-Andritz (AT); Stephan Winkler, Bochum (DE); Witold Michta, Remscheid (DE)

(73) Assignee: AVL List GmbH, Graz (AT)

(*) Notice: Subject to any disclaimer, the term of this patent is extended or adjusted under 35 U.S.C. 154(b) by 658 days.

(21) Appl. No.: 12/656,711

(22) Filed: Feb. 12, 2010

(65) Prior Publication Data

US 2010/0206251 A1 Aug. 19, 2010

(30) Foreign Application Priority Data

Feb. 12, 2009 (AT) .................................. A 238/2009

(51) Int. Cl.
*F02F 1/10* (2006.01)

(52) U.S. Cl.
USPC .................................. 123/41.72; 123/41.82 R

(58) Field of Classification Search
USPC .......... 123/193.2, 193.3, 193.5, 41.28, 41.29, 123/41.31, 41.72, 41.74, 41.75, 41.76, 41.82 R, 123/41.85
See application file for complete search history.

(56) References Cited

U.S. PATENT DOCUMENTS

| | | | | |
|---|---|---|---|---|
| 2,188,876 A | * | 1/1940 | Fahlman | 123/41.28 |
| 3,385,273 A | * | 5/1968 | Baster | 123/41.74 |
| 4,212,270 A | * | 7/1980 | Nakanishi et al. | 123/41.09 |
| 4,369,738 A | * | 1/1983 | Hirayama | 123/41.1 |
| 4,370,950 A | | 2/1983 | Furukubo | |
| 4,539,942 A | * | 9/1985 | Kobayashi et al. | 123/41.1 |
| 4,726,324 A | * | 2/1988 | Itakura | 123/41.1 |
| 4,726,325 A | * | 2/1988 | Itakura | 123/41.1 |
| 6,202,603 B1 | * | 3/2001 | Etemad | 123/41.74 |
| 6,823,823 B2 | * | 11/2004 | Kim | 123/41.74 |

FOREIGN PATENT DOCUMENTS

| | | |
|---|---|---|
| DE | 19628542 | 1/1998 |
| JP | 57146010 | 9/1982 |
| JP | 60019912 | 2/1985 |
| JP | 63016122 | 1/1988 |
| JP | 5256131 | 10/1993 |

OTHER PUBLICATIONS

English Abstract of DE19628542.
English Abstract of JP60019912.
English Abstract of JP57146010.
English Abstract of JP5256131.
English Abstract of JP63016122.

* cited by examiner

*Primary Examiner* — Noah Kamen
*Assistant Examiner* — Hung Q Nguyen
(74) *Attorney, Agent, or Firm* — Dykema Gossett PLLC

(57) ABSTRACT

An internal combustion engine includes a cylinder block and a cylinder head, with at least one first cooling jacket (1) being arranged in the cylinder block and at least one second cooling jacket (2) being arranged in the cylinder head, and a cooling fluid can flow through the cooling jackets (1, 2) substantially in the longitudinal direction of the internal combustion engine, and with both the cylinder block and the cylinder head having separate inflows (6, 8) and outlets (7, 9) for the cooling fluid which communicate with the respective cooling jacket (1, 2) in the cylinder block and cylinder head. In order to ensure even cooling especially of thermally loaded regions of the cylinder head, at least one flow transfer (10, 11) is arranged between the first cooling jacket (1) of the cylinder block and the second cooling jacket (2) of the cylinder head.

10 Claims, 2 Drawing Sheets

INTERNAL COMBUSTION ENGINE WITH A CYLINDER BLOCK AND A CYLINDER HEAD

BACKGROUND OF THE INVENTION

1. Field of the Invention

The invention relates to an internal combustion engine, comprising a cylinder block and a cylinder head, with at least one first cooling jacket being arranged in the cylinder block, and at least one second cooling jacket being arranged in the cylinder head and a cooling fluid can flow through the cooling jackets substantially in the longitudinal direction of the internal combustion engine, and with both the cylinder block as well as the cylinder head having separate inflows and outlets for the cooling fluid which communicate with the respective cooling jacket in the cylinder block and cylinder head. The invention further relates to a method for operating this internal combustion engine.

2. The Prior Art

It is known to cool the cylinder block and the cylinder head of an internal combustion engine by a cooling circuit which usually contains water which is guided to the radiator after passing through the engine in order to bring the cooling water there to a lower temperature. It is also known to arrange a pump in the cooling circuit. It has been noticed in internal combustion engines that the cylinder head needs to be cooled more strongly than the cylinder block which, as is known, is subjected to lower thermal loads. This is considered in the known cooling systems only in such a way that one forces a relatively large amount of cooling fluid through the cylinder head to the thermally critical regions in that the entire coolant quantity is allowed to flow from the cylinder block through geometrically limited passages through the cylinder head gasket, which inevitably leads to high pressure drops.

In the case of cooling chambers in the cylinder head with longitudinal flow which are connected with the cooling chambers of the cylinder block via passages, there is a disadvantage that the first cylinder is cooled worse than the cylinders which are arranged downstream in the cooling circuit of the cylinder head because the cooling jacket of the cylinder head acts as a collecting element and the accumulation of the coolant quantity leads to higher flow speeds with each cylinder and thus leads to better cooling effects on the one hand but also causes an increasing pressure difference along the cooling jacket on the other hand. This significant pressure difference along the engine requires a compensating, oppositely directed and clear gradation of the passages through the cylinder head gasket, leading inevitably to very small dimensions of the smallest gasket passages, which is why the total pressure drop typically can reach high unfavorable magnitudes in order to provide acceptable cooling conditions also for the first cylinder. Furthermore, flow through thermally critical regions which are substantially oriented transversally to the longitudinal direction of the engine, especially in the region of the exhaust valve seat, is adverse as a result of the inexistent pressure difference transversally to the engine, with the critical regions not being cooled optimally.

It is further known to use separate cooling circuits for cylinder block and cylinder head. A cooling system for an internal combustion engine is known for example from DE 196 28 542 A1, in which the cylinder head is cooled by a first cooling water circuit and the cylinder block by a second cooling water circuit, with the cylinder head and cylinder block being flowed through in parallel. An improved cooling of the cylinder head can thus be achieved. Internal combustion engines with divided cooling circuits are further also known from the publications JP 60 019 912 A2, JP 57 146 010 A2 or U.S. Pat. No. 4,370,950 A. Even in the case of internal combustion engines with divided cooling circuits, thermally critical regions which are substantially oriented transversally to the longitudinal direction of the engine show adverse flow as a result of the inexistent pressure difference and are thus not cooled optimally.

It is the object of the invention to avoid these disadvantages and to achieve an even and optimal cooling in combination with acceptable pressure drops and minimization of parallel flows in an internal combustion engine of the kind mentioned above.

SUMMARY OF THE INVENTION

This is achieved in accordance with the invention in such a way that at least one flow transfer is arranged between the first cooling jacket of the cylinder block and the second cooling jacket of the cylinder head, with preferably the flow transfer being arranged in the region of a common boundary surface between cylinder block and cylinder head, preferably in the region of the cylinder head sealing surface. It is especially advantageous when the inflow and outlet openings of the cylinder block and/or the cylinder head are arranged at opposite ends of the cylinder block or cylinder head.

The basic idea of the invention thus lies in the combination of the advantages of the even flow and cooling situation by applying two substantially separated cooling chambers with longitudinal flow (the first cylinder receives approximately the same cooling quantity as the last cylinder) and minimum local coolant supply of the flow passages (e.g. between exhaust valve seat rings) which are oriented transversally to the direction of the main flow through the flow transfers which are arranged in the cylinder head gasket for example.

In order to sufficiently cool especially the intermediate cylinder region in the cylinder block and the wedge region between two adjacent cylinders in the cylinder head, it is advantageous when at least one first flow transfer is arranged in the region of a first transverse engine plane between two adjacent cylinders.

An especially good heat dissipation from thermally critical regions around the exhaust valve seat rings can be effected when at least one second flow transfer is arranged in the region of a second transversal engine plane which contains at least one cylinder axis, with the second flow transfer preferably leading to a cooling region between two exhaust valve seat rings.

Practical tests have shown that a considerable improvement of the cooling can be achieved when the cross sections of all flow transfers are dimensioned in such a way that a maximum of 20%, preferably not more than 15%, of the entire cooling fluid supplied to the cylinder block and cylinder head flow from the engine block into the cylinder head, with preferably at least 10% of the entire cooling fluid quantity supplied to the cylinder block and the cylinder head flowing from the motor block to the cylinder head.

An even cooling over the entire length of the cylinder block can be achieved when the flow transfers, preferably the second flow transfers, have differently large flow cross sections, with the flow cross sections of the flow transfers being smaller in the region of the first end than in the region of the second end.

BRIEF DESCRIPTION OF THE DRAWINGS

The invention will now be explained in greater detail by reference to the drawings, wherein.

DETAILED DESCRIPTION OF THE PREFERRED EMBODIMENT

Figure 1:
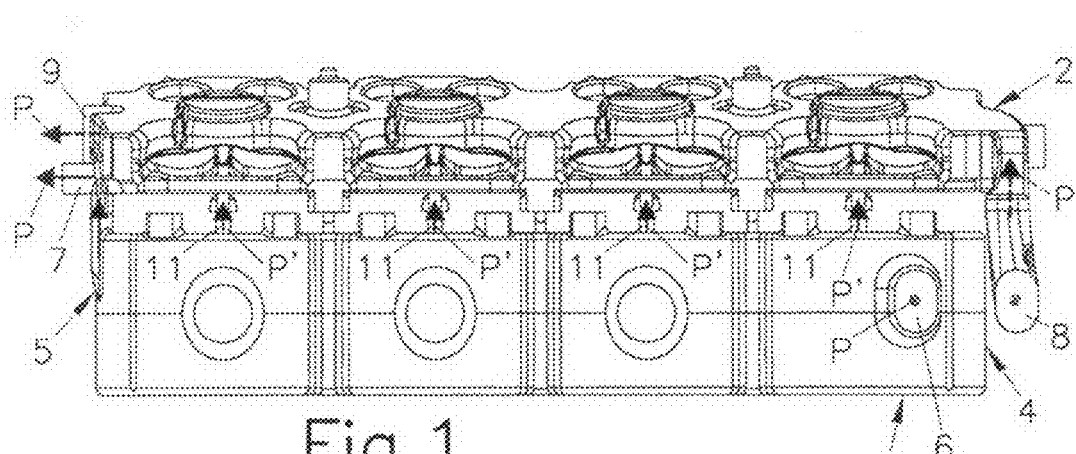
FIG. 1 shows a side view of a cooling jacket of an internal combustion engine in accordance with the invention.
Figure 2:
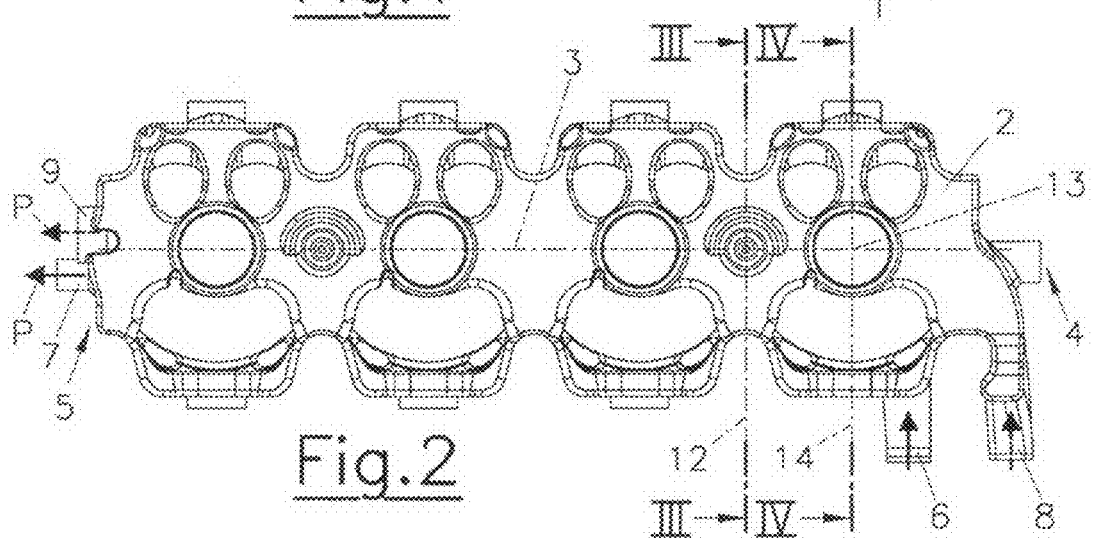
FIG. 2 shows a top view of the cooling jacket.
Figure 3:
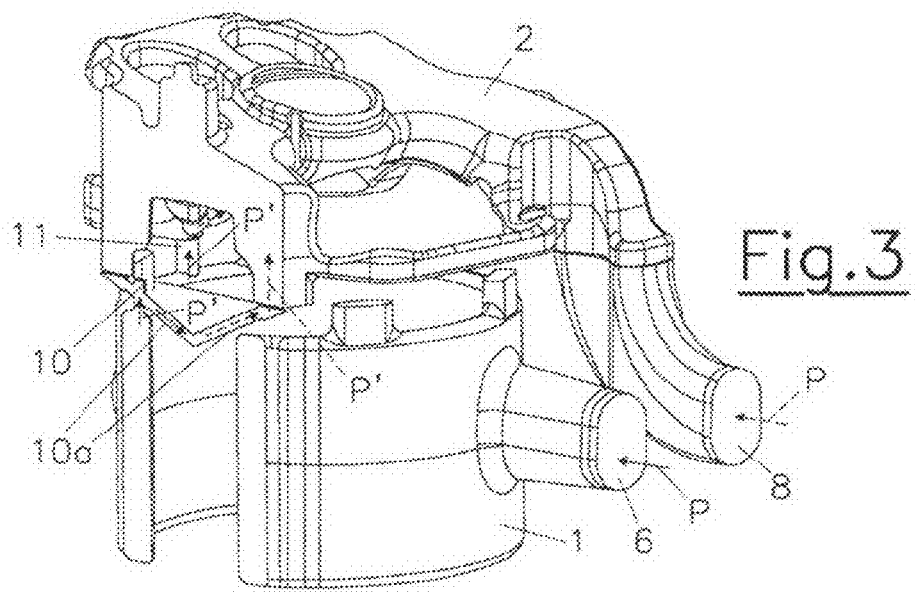
FIG. 3 shows the cooling jacket in an oblique sectional view along the line in FIG. 2.
Figure 4:
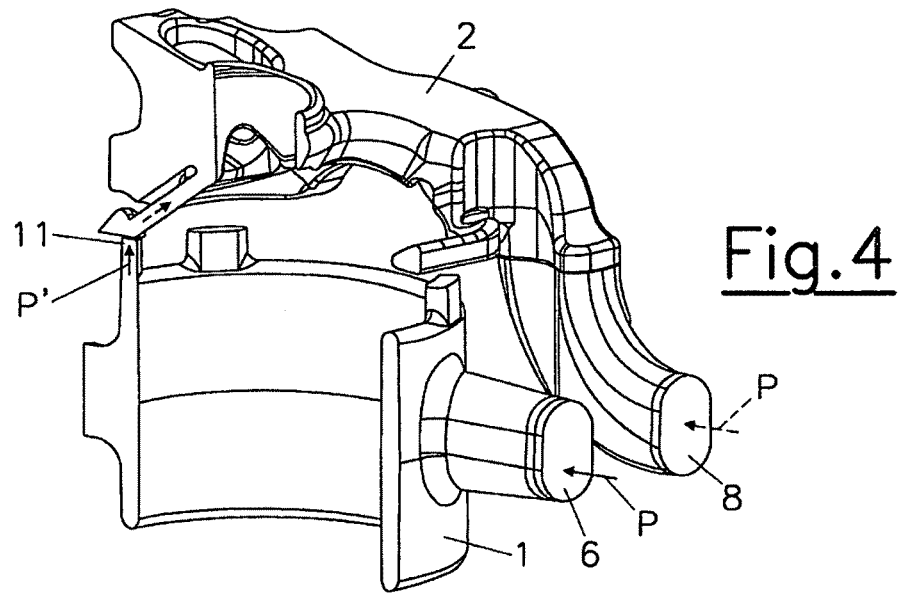
FIG. 4 shows the cooling jacket in an oblique sectional view along the line IV-IV in FIG. 2.

The internal combustion engine comprises a first cooling jacket 1 in the cylinder block and a second cooling jacket 2 in the cylinder head, with the flow moving through the two cooling jackets 1, 2 substantially in the direction of the longitudinal axis 3 of the internal combustion engine between a first end 4 and a second end 5. The first cooling jacket 1 of the cylinder block comprises an inflow 6 at the first end 4 and an outlet 7 in the region of the second end 5. Furthermore, the second cooling jacket 2 of the cylinder head also comprises an inflow 8 at the first end 4 of the internal combustion engine and an outlet 9 at the second end. The flow moves through the first and second cooling jacket 1, 2 in a separate and substantially parallel manner according to the arrows P. In order to enable an even cooling of all cylinders on the one hand and a purposeful dissipation of heat from thermally highly loaded regions on the other hand, a small partial flow of approx. 10% to 20% of the entire cooling fluid quantity on which the internal combustion engine is based is guided from the first cooling jacket 1 into the second cooling jacket 2, with the cooling fluid reaching via first and second flow transfers 10, 11 from the first cooling jacket 1 into the second cooling jacket 2.

The first flow transfers 10 are arranged between two cylinders in the region of the first transversal engine planes 12, whereby drilled connection ports 10a which are arranged in a substantially V-shaped manner can be provided in the region of the first transversal engine plane 12. The first flow transfers 10 are used for cooling the intermediate cylinder area in the cylinder block and the wedge-like region of the cylinder head between two cylinders each.

The second flow transfers 11 are each arranged on the outlet side in the region of a second transversal engine plane 14 extending through the cylinder axis 13 and are used for cooling the exhaust valve seat rings. As a result of the missing pressure difference transversally to the main direction of flow (along the cylinder axis 13), an individual supply is urgently required for the through-flow of this flow passage between the exhaust valve seat rings.

Figure 5:
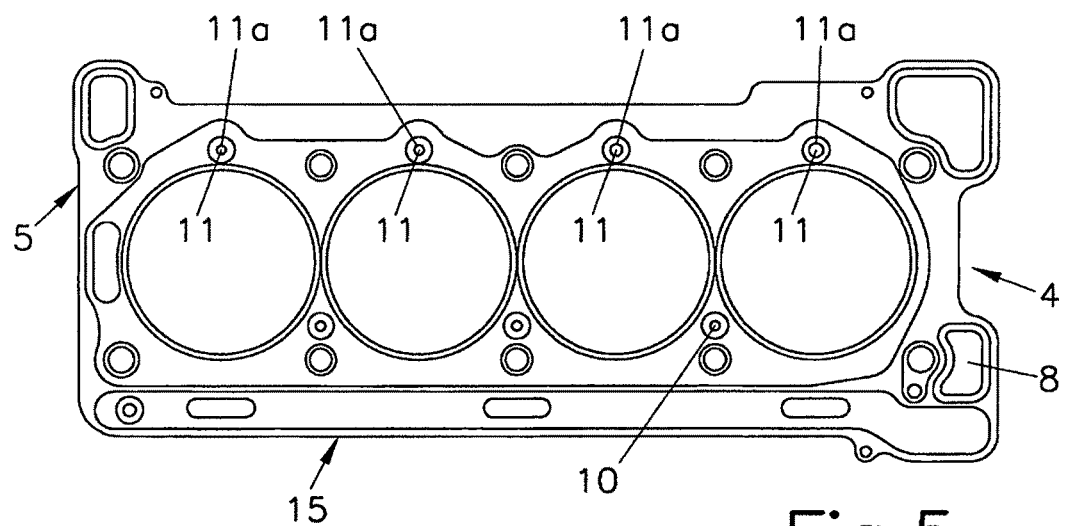
FIG. 5 shows a top view of a cylinder head gasket of the internal combustion engine in accordance with the invention.

As is shown in FIG. 5, the second flow transfers have differently large flow cross sections depending on the cylinder, with the flow cross sections in the region of the first end 4 being larger than in the region of the second end 5 of the internal combustion engine. The different flow cross sections are formed by differently large openings 11a in the cylinder head gasket 15. The different flow cross sections of the second flow transfers 11 ensure that the cylinder head is evenly cooled between the first end 4 and the second end 5, so that sufficient heat dissipation is also ensured for the last cylinder arranged close to the outlet 9.

The cooling fluid reaches the cooling jackets 1,2 of the cylinder block and cylinder head of the internal combustion engine via the inflows 6, 8 according to arrows P and flows through the same parallel to the longitudinal axis 3. A small portion of the cooling fluid of the first cooling jacket 1 flows via the first and second flow transfers 10, 11 into the second cooling jacket according to the arrows P'. The cooling fluid leaves the first cooling jacket 1 and the second cooling jacket 2 via the outlets 7 and 9.

The invention claimed is:

1. An internal combustion engine, comprising a cylinder block and a cylinder head, with a first cooling jacket in the cylinder block and a second cooling jacket in the cylinder head, means forming separate cooling fluid inflows to and outlets from the respective first cooling jacket in the cylinder block and second cooling jacket in the cylinder head so that cooling fluid separately flows through the first and second cooling jackets in a longitudinal direction of the engine, and including means forming a flow transfer channel between the first cooling jacket of the cylinder block and the second cooling jacket of the cylinder head.

2. The internal combustion engine according to claim 1, wherein the means forming a flow transfer channel is located in a region of a common boundary surface between said cylinder block and said cylinder head.

3. The internal combustion engine according to claim 1, wherein the means forming inflows to and outlets from the cylinder block and/or the cylinder head are respectively located at opposite ends of the cylinder block or cylinder head.

4. The internal combustion engine according to claim 1, a first means forming a flow transfer channel is located in a region of a first transverse engine plane between two adjacent cylinders.

5. The internal combustion engine according to claim 1, a second means forming a flow transfer channel is located in a region of a second transversal engine plane which contains at least one cylinder axis, with the second means forming a flow transfer channel leading to a cooling region between two exhaust valve seat rings.

6. The internal combustion engine according to claim 1, wherein cross sections of all means forming flow transfer channels are dimensioned such that a maximum of 20% of a totality of cooling fluid supplied to the cylinder block and cylinder head flows from the engine block into the cylinder head.

7. The internal combustion engine according to claim 6, wherein said cross sections of all means forming flow transfer channels are dimensioned such that no more than 15% of the entire cooling fluid supplied to the cylinder block and cylinder head flow from the engine block into the cylinder head.

8. The internal combustion engine according to claim 1, wherein cross sections of all means forming flow transfer channels are dimensioned such that a minimum of 10% of a totality of cooling fluid supplied to the cylinder block and cylinder head flow from the engine block into the cylinder head.

9. The internal combustion engine according to claim 1, wherein at least two second means forming flow transfer channels have differently large flow cross sections, with the flow cross sections of the flow transfer channels being larger in a region of the first end than in a region of the second end.

10. The internal combustion engine according to claim 9, wherein the different flow cross sections are formed by differently large openings in a cylinder head gasket arranged between cylinder block and cylinder head.

* * * * *